(12) United States Patent
Xu et al.

(10) Patent No.: US 9,283,281 B2
(45) Date of Patent: Mar. 15, 2016

(54) PREPARATION OF TRIPLE RESPONSIVE NANOGEL SYSTEM AND ITS APPLICATION

(71) Applicants: Peisheng Xu, Chapin, SC (US); Huacheng He, West Columbia, SC (US)

(72) Inventors: Peisheng Xu, Chapin, SC (US); Huacheng He, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/330,336

(22) Filed: Jul. 14, 2014

(65) Prior Publication Data

US 2015/0018308 A1    Jan. 15, 2015

Related U.S. Application Data

(60) Provisional application No. 61/845,609, filed on Jul. 12, 2013.

(51) Int. Cl.
| | |
|---|---|
| C08F 220/68 | (2006.01) |
| A61K 47/32 | (2006.01) |
| A61K 41/00 | (2006.01) |
| A61K 31/695 | (2006.01) |

(52) U.S. Cl.
CPC .............. *A61K 47/32* (2013.01); *A61K 31/695* (2013.01); *A61K 41/0057* (2013.01); *C08F 220/68* (2013.01)

(58) Field of Classification Search
CPC ...... C08F 220/68; A61K 47/32; A61K 41/00; A61K 31/695
See application file for complete search history.

(56) References Cited

U.S. PATENT DOCUMENTS

| | | | | |
|---|---|---|---|---|
| 6,491,903 | B1 * | 12/2002 | Forster ..................... | C08J 3/246 424/489 |
| 2003/0152623 | A1 * | 8/2003 | Bromberg .............. | A61K 8/042 424/468 |

* cited by examiner

*Primary Examiner* — Robert Harlan

(57) ABSTRACT

A thermal triple-responsive polymer, along with methods of its formation and use, is generally provided. The thermal triple-responsive polymer can comprise poly[(2-(pyridin-2-yldisulfanyl)-co-[poly(ethylene glycol)]-co-[N-isopropyl methacrylamide], which contains both disulfide bonds and ester bonds that are labile to high redox potential and acidic pH, respectively, and temperature sensitive segments. The thermal triple-responsive polymer can be modified with 4-methoxybenzoic acid to endow tumor targeting effect. Nanoparticles and nanogels that include such a thermal triple-responsive polymer are also provided, along with their methods of formation and use.

14 Claims, 12 Drawing Sheets

PREPARATION OF TRIPLE RESPONSIVE NANOGEL SYSTEM AND ITS APPLICATION

PRIORITY INFORMATION

The present application claims priority to U.S. Provisional Patent Application Ser. No. 61/845,609 titled "Preparation of Triple Responsive Nanogel System and its Application" of Xu, et al. filed on Jul. 12, 2013, the disclosure of which is incorporated by reference herein.

BACKGROUND

Photodynamic therapy (PDT) is a treatment procedure that uses a light to activate a photosensitizer (PS) to produce singlet oxygen for killing cancer cells or curing acne. Since the onset of PS toxicity can only be triggered by the irradiation of light, PDT generally is considered as a safe alternative for chemotherapy in the treatment of cancer, and does not induce side effects. A lot of evidences indicate that PDT-induced apoptosis is due to the damage of mitochondria and suggest that mitochondria are the target for PDT. Therefore, the efficacy of PS would be greatly enhanced if it can be delivered specifically to the mitochondria of cancer cells. In fact, research revealed that Pc 4 (a silicon phthalocyanine photosensitizer) can spontaneously partition to mitochondria due to its high hydrophobicity, which makes it an ideal PS for maximizing PDT efficacy. However, the clinical application of Pc 4 based PDT has not been widely accepted due to its poor water solubility and erratic tissue retention, especially in the skin which results in unwanted tissue damage upon the exposure to sunshine.

Additionally, much effort has been devoted to the development of PDT for head and neck cancers. However, PDT still has not been widely accepted due to its potential skin toxicity upon exposure to light, low efficiency as a result of low solubility and aggregation of the photosensitizer (PS). A carrier system that can fully take advantage of the benefits of PDT while minimizing its side effects is urgently needed.

Over past decades, many types of nanoparticle carriers have been developed for targeted delivery of Pc 4 to tumor by taking advantage of the leaky vascular structure in tumor tissue through so called enhanced permeability and retention (EPR) effect. Such systems include polymeric micelles, mesoporous silica nanoparticles, and gold nanoparticles, which can load hydrophobic Pc 4 through hydrophobic interaction. Although with the help of various ligand-receptor interactions most nanoparticles achieved enhanced cellular uptake of Pc 4, there was occasional disconnection between the uptake of PS and their PDT efficacy. Higher uptake of PS did not result in better cell killing, possibly due to the fact that those encapsulated Pc 4 could not effectively escape from lysosome and then transfer to mitochondria.

SUMMARY

Objects and advantages of the invention will be set forth in part in the following description, or may be obvious from the description, or may be learned through practice of the invention.

A thermal triple-responsive polymer is generally provided, along with methods of its formation and use. In one embodiment, the thermal triple-responsive polymer comprises poly [(2-(pyridin-2-yldisulfanyl)-co-[poly(ethylene glycol)]-co-[N-isopropyl methacrylamide], which contains both disulfide bonds and ester bonds that are labile to high redox potential and acidic pH, respectively, and temperature sensitive segments. In one particular embodiment, the thermal triple-responsive polymer is modified with 4-methoxybenzoic acid to endow tumor targeting effect.

Nanoparticles and nanogels that include such a thermal triple-responsive polymer are also provided, along with their methods of formation and use. For example, a photosensitizer loaded nanogel is generally provided in one embodiment that includes the thermal triple-responsive polymer and a photosensitizer.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DEFINITIONS

Figure 1A:
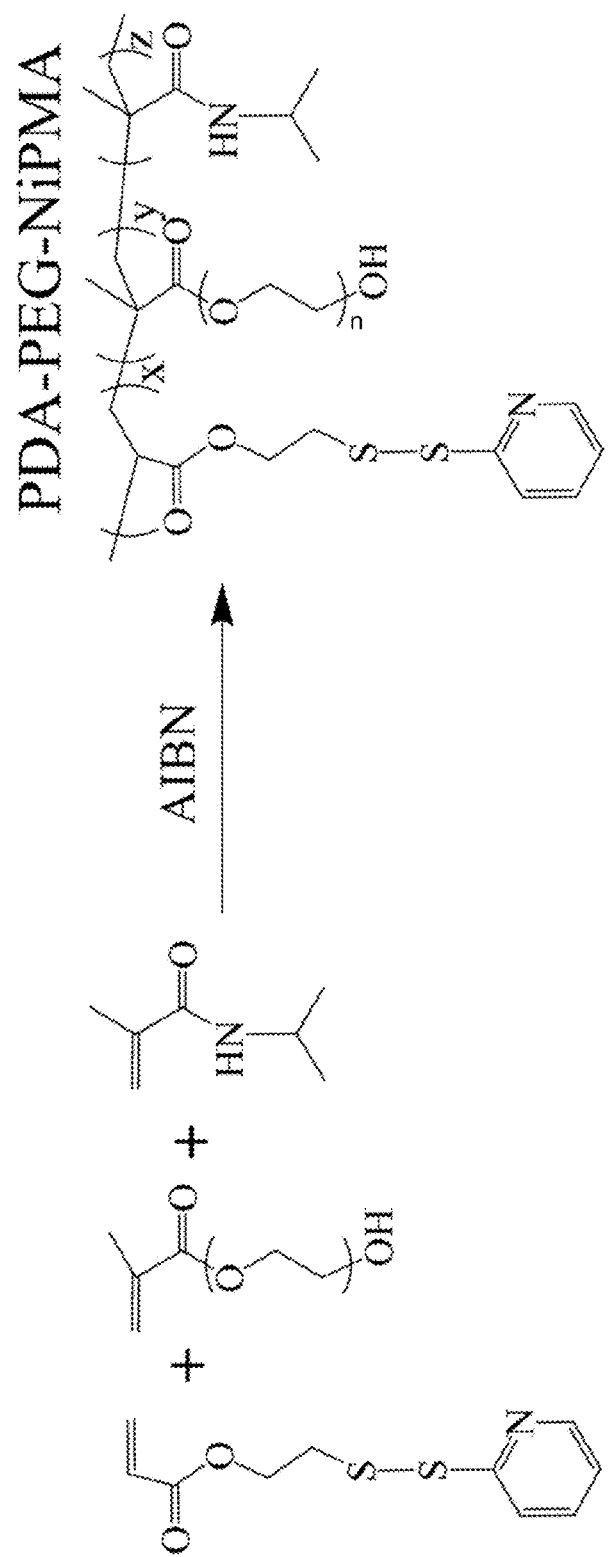
FIG. 1A shows a schematic illustration of the synthesis of an exemplary PDA-PEG-NiPMA polymer.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\tilde{M}_n = \frac{\sum_i N_i M_i}{\sum_i N_i}$$

where $N_i$ is the number of molecules of molecular weight $M_i$. The number average molecular weight of a polymer can be determined by gel permeation chromatography, viscometry (Mark-Houwink equation), and all colligative methods, like vapor pressure osmometry or end-group determination.

The "weight average molecular weight" ($M_w$) is readily calculated by one of ordinary skill in the art, and generally refers to:

$$\tilde{M}_w = \frac{\sum_i N_i M_i^2}{\sum_i N_i M_i}$$

where $N_i$ is the number of molecules of molecular weight $M_i$. The weight average molecular weight can be determined by light scattering, small angle neutron scattering (SANS), X-ray scattering, and sedimentation velocity.

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

The term "pharmaceutically effective amount" refers to that amount of a drug or pharmaceutical agent that will elicit the biological or medical response of a tissue, system, animal, or human that is being sought by a researcher or clinician. This amount can be a therapeutically effective amount.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

A pH, thermal, and redox potential triple-responsive expansile nanogel system (TRN), which swells at acidic pH, temperature higher than its transition temperature, and reducing environment, is generally provided. In one embodiment, the thermal triple-responsive polymer comprises poly[(2-(pyridin-2-yldisulfanyl)-co-[poly(ethylene glycol)]-co-[N-isopropyl methacrylamide], which contains both disulfide bonds and ester bonds that are labile to high redox potential and acidic pH, respectively, and temperature sensitive segments. For example, the thermal triple-responsive polymer can have the structure:

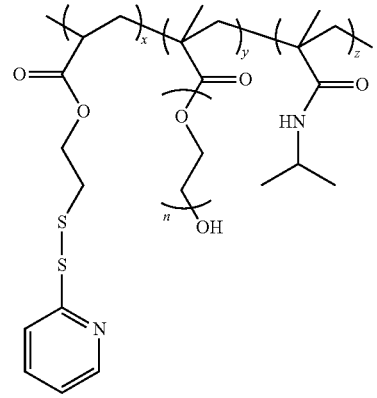

where x is about 3 to about 500; y is about 3 to about 500; n is about 3 to about 200; and z is about 3 to about 500. It is to be understood that the structure shown above is intended to be a generic type of copolymer, and includes configurations such as block copolymers, graft copolymers, random copolymers, and/or alternating copolymers.

Such a thermal triple-responsive polymer can be generally formed via free radical polymerization of 2(pyridin-2-yldisulfanyl)ethyl acrylate, poly(ethylene glycol) methacrylate, and N-isopropyl methacrylamide with an initiator (e.g., 2,2-azobisisobutyronitrile), as shown in FIG. 1A. For example, methods of free radical polymerization are disclosed in U.S. Publication No. 2012/0041163 of Tang, et al., which is incorporated by reference herein.

The thermal triple-responsive polymer has, in one embodiment, a weight average molecular weight of about 5,000 Da to about 500,000 Da and/or a polydispersity of about 1.1 to about 2.5.

Figure 1B:
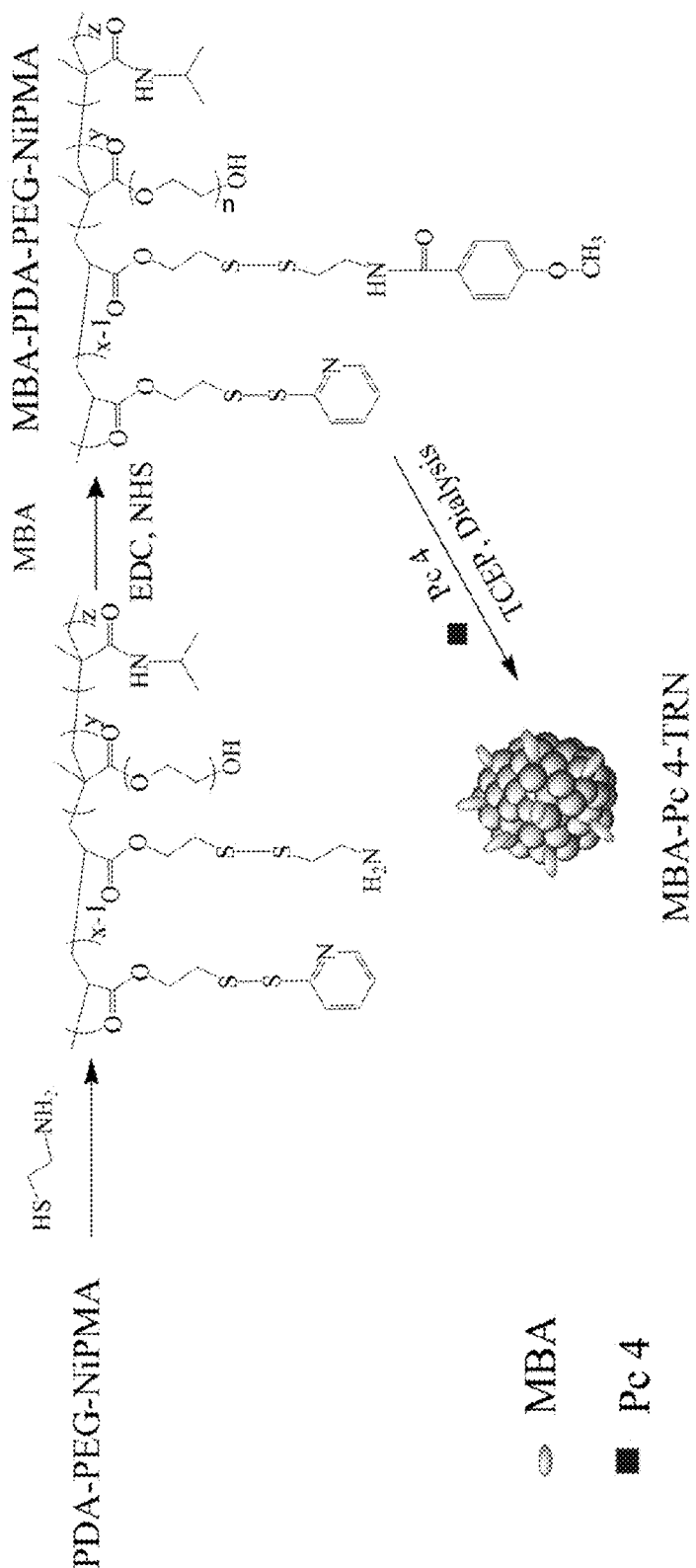
FIG. 1B shows a schematic illustration of the fabrication of an exemplary MBA-Pc 4-TRN nanogel, using the PDA-PEG-NiPMA polymer formed via FIG. 1A.

In one embodiment, the thermal triple-responsive polymer comprises poly[(2-(pyridin-2-yldisulfanyl)-co-[poly(ethylene glycol)]-co-[N-isopropyl methacrylamide], as described above, modified with 4-methoxybenzoic acid to endow tumor targeting effect, such as shown in FIG. 1B. For example, the thermal triple-responsive polymer can have the structure:

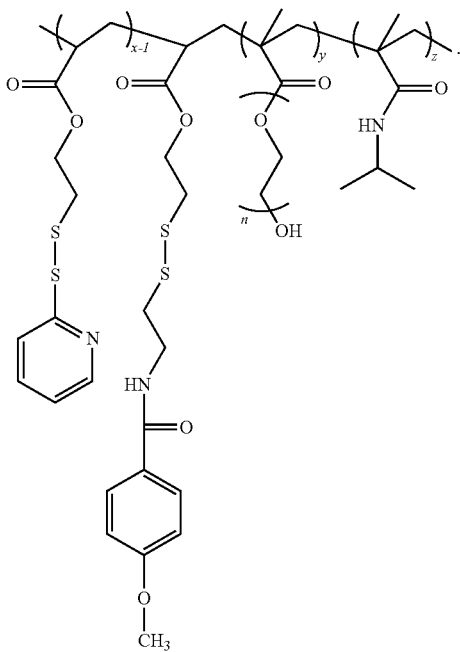

It is to be understood that the structure shown above is intended to be a generic type of copolymer, and includes configurations such as block copolymers, graft copolymers, random copolymers, and/or alternating copolymers.

A photosensitizer loaded nanogel is also generally provided that includes the thermal triple-responsive polymer, such as described above, and a photosensitizer. The nanogel is formed, in one embodiment, through reaction of a thermal triple-responsive polymer with a crosslinker and a photosensitizer.

Such a nanogel and/or nanoparticle can be administered to a subject having a tumor in a pharmaceutically effective amount to treat (via killing with selectivity) tumor cells.

EXAMPLES

The goal of this study was to develop a phthalocyanine Pc 4-loaded nanoparticle that selectively targets tumor tissue and is capable of self-expanding to release its payload when triggered by acidic lysosomal pH and elevated intralysosomal redox potential. pH, redox potential, and thermal triple-responsive nanoparticles (TRN) were prepared by dialysis of a poly[(2-(pyridin-2-yldisulfanyl)-co-[poly(ethylene glycol)]-co-[N-isopropyl methacrylamide]/Pc 4 mixture after crosslinking initiated by tris(2-carboxyethyl)phosphine. Loading efficiency of Pc 4 was 38.6% and the size of the Pc 4-TRN was 98.6±0.6 nm as determined by dynamic scattering. Pc 4-TRN size increased with increasing redox potential or temperature and decreasing pH in vitro. Confocal microscopy revealed Pc 4-TRN are taken up by cancer cells and transferred to endosomes/lysosomes, they self-expand and eventually degrade in an acidic environment, resulting in breakage of lysosomal membranes to allow free Pc 4 to be released from lysosomes and transported to mitochondria. After irradiation, Pc 4-TRN induced greater cell killing compared to Pc 4 (100% vs. 35% after 5 h of PDT). Furthermore, in vivo experiment shown that MBA-Pc 4-TRN could specifically target to the tumor tissue.

It has been found that the TRN can quickly expand from 108 nm to over 1200 nm (in diameter), achieving more than 1000-fold size enlargement (in volume), within 2 h in a reducing environment at body temperature. Sigma-2 receptor targeting-ligand functionalized TRN can effectively target head and neck tumor, and help Pc 4 targeting mitochondria inside cancer cells to achieve enhanced photodynamic therapy efficacy. Therefore, a nanocarrier which can escape from lysosome, quickly expand its size to release Pc 4 into cytosol is able to deliver Pc 4 to mitochondria. Expansile nanoparticles (eNP), which can enlarge their size in response to pH, have been explored as drug carriers to control the drug release at targeted sites and achieved enhanced therapeutic effect. Nanogels fabricated from pyridyl disulfide containing polymers have been applied in various drug delivery systems due to their easy functionalization. Recently, our group reported a multicompartment nanogel made of poly[(2-(pyridin-2-yldisulfanyl)-co-[poly(ethylene glycol)]] (PDA-PEG) polymer, which showed self-expanding property in reducing environment and size increasing from 115 nm to 262 nm in 5 h. In addition, the release of its payload was dependent on its environmental pH and redox potential. The abundance of pyridine segments endowed the proton sponge effect of the polymer and helped its escaping from lysosome.

To extend the sensitiveness of the nanogel to temperature, a thermal responsive polymer, poly(N-Isopropyl methacrylamide) (PNiPMA), was incorporated into the PDA-PEG by free radical polymerization to yield a pH, redox potential, and thermal triple-responsive polymer PDA-PEG-PNiPMA as described in FIG. 1A. A triple-responsive nanogel (TRN) was fabricated with the help of predesigned amounts of tris(2-carboxyethyl)phosphine (TCEP).

Example 1

A. Experimental

Aldrithiol-2 and Silica gel (Spherical, 100 μm) were purchased from Tokyo Chemical Industry Co., LTD (Harborgate Street, Portland, Oreg.). 2-mercaptoethenol, DL-dithiothreitol (DTT), tris(2-carboxyethyl)phosphine (TCEP), 2,2-Azobisisobutyronitrile (AIBN) and Poly(ethylene glycol)methacrylate (Mn=360 Da) were purchased from Sigma-Aldrich Chemical Co. (St. Louis, Mo.). Penicillin (10,000 U/mL), streptomycin (10,000 μg/mL), 0.25% trypsin-EDTA, Dulbecco's Modified Eagle Medium (with L-glutamine) and fetal bovine serum (FBS) were obtained from American Type Culture Collection (ATCC, Manassas, Va.). 2,4,6-Trinitrobenzene sulfonic acid (TNBSA) was purchased from Thermo Scientific. Silicon phthalocyanine (Pc 4) was acquired from NCI (NSC 676418). All the other solvents used in this research were purchased from Sigma-Aldrich Chemical Co. (St. Louis, Mo.) and used without further purification unless otherwise noted.

I. Synthesis of poly[(2-(pyridin-2-yldisulfanyl)-co-[poly(ethylene glycol)]-co-[N-isopropyl methacrylamide] (PDA-PEG-NiPMA)

PDA-PEG-NiPMA polymer, which contains both disulfide bonds and ester bonds that are labile to high redox potential and acidic pH, respectively, and temperature sensitive segments was synthesized by free radical polymerization of 2(pyridin-2-yldisulfanyl)ethyl acrylate (PDA), poly(ethylene glycol) methacrylate (PEG) (MW 360 Da), and N-isopropyl methacrylamide using 2,2-azobisisobutyronitrile (AIBN) as an initiator (FIG. 1A). Typically, PDA (241.3 mg, 1 mmol), PEG360 (360 g, 1 mmol) and N-Isopropylmethacrylamide (NiPMA, 63.6 mg, 0.5 mmol) were dissolved in 10 mL degassed anisole. 2,2-azobisisobutyronitrile (AIBN, 14 mg, 0.085 mmol) in 1 mL degassed anisole was then added, and the reaction mixture was stirred for 24 hours at 65° C. The final product was precipitated (3×) in ice cold ether and dried for 48 hours in vacuum.

The structure of PDA-PEG-PNiPMA was confirmed by $^1$H-NMR. Gel permeation chromatography (viscotek GPC-max VE 2001 GPC solvent/sample module, Viscotek VE 3580 RI detector and 270 Dual Detector) using THF as mobile phase was employed to characterize the polymer and found PDA-PEG-PNiPMA has an absolute molecular weight of 27,557 Da (Mw) and polydispersity (PDI: 1.35).

For the quantification of side chain functionality, PDA-PEG-PNiPMA (1.0 mg/mL) was dissolved in DMSO and incubated with dithiothreitol (DTT, 10 mM) for 1 hour at room temperature, and then the amount of 2-pyridinethione released was quantified through UV-Vis spectrophotometer at $\lambda=375$ nm ($\epsilon$, molar absorption coefficient=8080 M$^{-1}$ cm$^{-1}$).

II. PS Pc 4 Loaded PDA-PEG-NiPMA Nanogel

Briefly, Pc4 (5%, 250 µg) was firstly dissolved in 100 µL DMSO and then added into PDA-PEG-NiPMA DMSO solution (5 mg polymer in 250 µL DMSO) or MBA-PDA-PEG-NiPMA reaction solution (5 mg polymer in DMSO), following the addition of tris(2-carboxyethyl)phosphine hydrochloride (TCEP, 0.384 mg in 20 µL DMSO, 30% cross-linking) The reaction mixture was equilibrated for 15 min and then dropped into 4 mL ddH$_2$O under stirring and kept stirring for aerial oxidation overnight. After the oxidation, the nanogel was then dialyzed towards PBS 7.4 (10 mM) for 4 hours to remove un-reacted TCEP and organic solvent. Finally, the nanogel was filtered (0.45 µm syringe filter) and stored in 4° C. The loading efficiency was quantified by measuring the absorbance at 675 nm.

III. MBA-PDA-PEG-NiPMA Nanogel Fabrication

PDA-PEG-NiPMA polymer was further modified with 4-methoxybenzoic acid (MBA) to endow tumor targeting effect (MBA is a sigma-2 receptor targeting motif). Briefly, cysteamine (0.404 mg, 20% PDA function group) in 500 µl methanol was added dropwise into 20 mg PDA-PEG-NiPMA in 500 µl dichloromethane. The reaction mixture was kept at room temperature overnight. Subsequently, 250 µl reaction solution was taken out and MBA (67.8 µg in 200 µl DMSO), N-hydroxysuccinimide (NHS, 102 µg in 10 µl DMSO) and ethyl(dimethylaminopropyl) carbodiimide (EDC, 171 µg in 10 µl DMSO) were added. After overnight reaction, the final reaction solution was dialyzed against DMSO using Spectra/Por® dialysis tube (MWCO: 1000 Da). The concentration of amine group in the polymer after dialysis was quantified by TNBSA assay. MBA (1.66 mg in 100 µL DMSO, 50% PDA function group) was firstly activated by EDC (4.2 mg in 50 µL DMSO) and NHS (2.5 mg in 50 µL DMSO), and then added into 20 mg cysteamine modified PDA-PEG-PNiPMA polymer. The reaction was kept overnight at room temperature. The amine concentration in PDA-PEG-PNiPMA polymer after MBA conjugation was also quantified by TNBSA assay to determine the MBA conjugation efficiency. TNBSA assay result revealed that 16% MBA (to PDA ratio) has been successfully conjugated to the polymer.

Then, the PDA-PEG-NiPMA polymer was used directly for nanogel fabrication through the method described above. Briefly, PDA-PEG-PNiPMA and MBA-PDA-PEG-PNiPMA were mixed to obtain different MBA ligand density for TRN. The polymer mixture (5 mg) was dissolved in 300 µL DMSO. Pc 4 (250 µg) was dissolved in 100 µL DMSO and then added into the polymer mixture. For the fabrication of TRN with 30% cross-linking density, tris(2-carboxyethyl)phosphine hydrochloride (TCEP, 0.384 mg in 20 µL DMSO) was added to the above mixture. The reaction mixture was equilibrated for 15 min and then dropped into 4 mL ddH$_2$O under stirring and kept stirring for aerial oxidation overnight. After the oxidation, the nanogel was then dialyzed towards PBS of pH 7.4 (10 mM) for 10 h to remove unreacted TCEP, MBA and organic solvent. Finally, the nanogel was filtered (0.45 µm syringe filter) and stored in 4° C. The morphology, size distribution and the surface charge ($\zeta$-potential), of the nanogel were determined by a Hitachi H8000 transmission electron microscopy (TEM) and dynamic light scattering (DLS).

B. Results

I. Triple Responsiveness of PDA-PEG-NiPMA

Figure 4A:
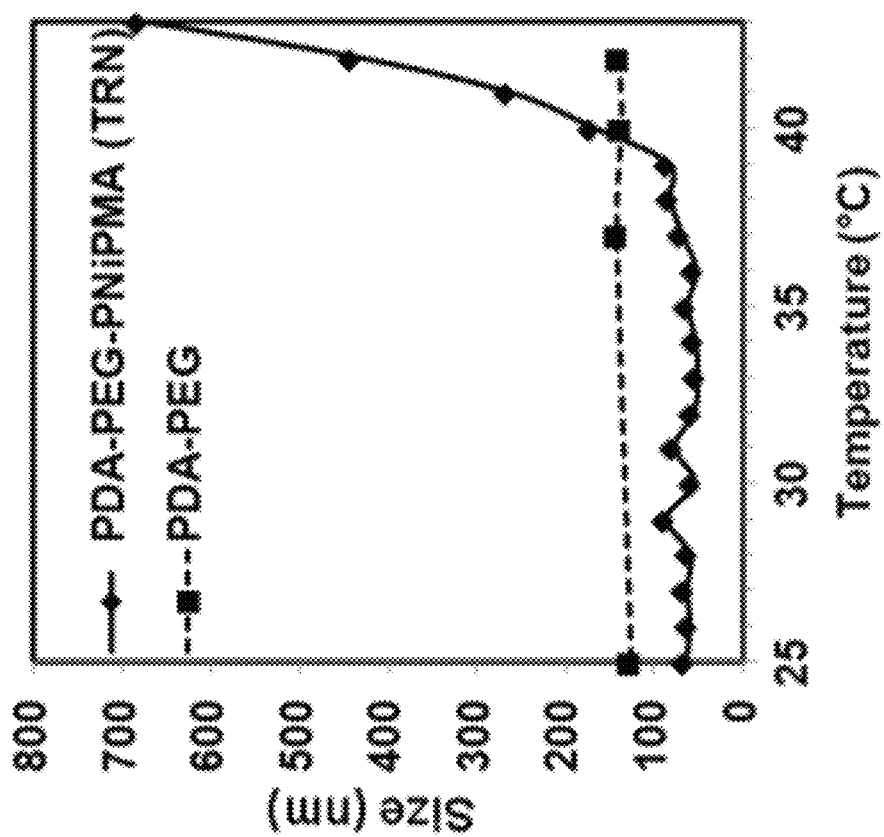
FIG. 4A shows the z-average size of TRN in response to the change of temperature, according to the Examples.
Figure 4B:
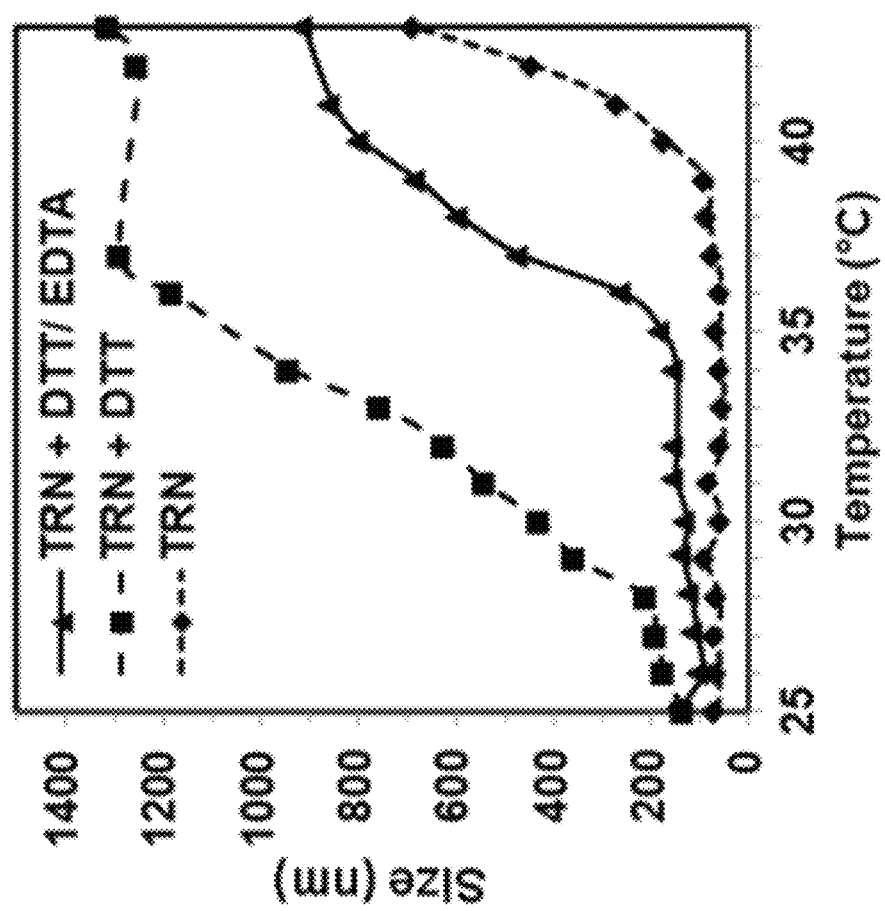
FIG. 4B shows the z-average size of TRN in response to the change of temperature, according to the Examples.
Figure 4C:
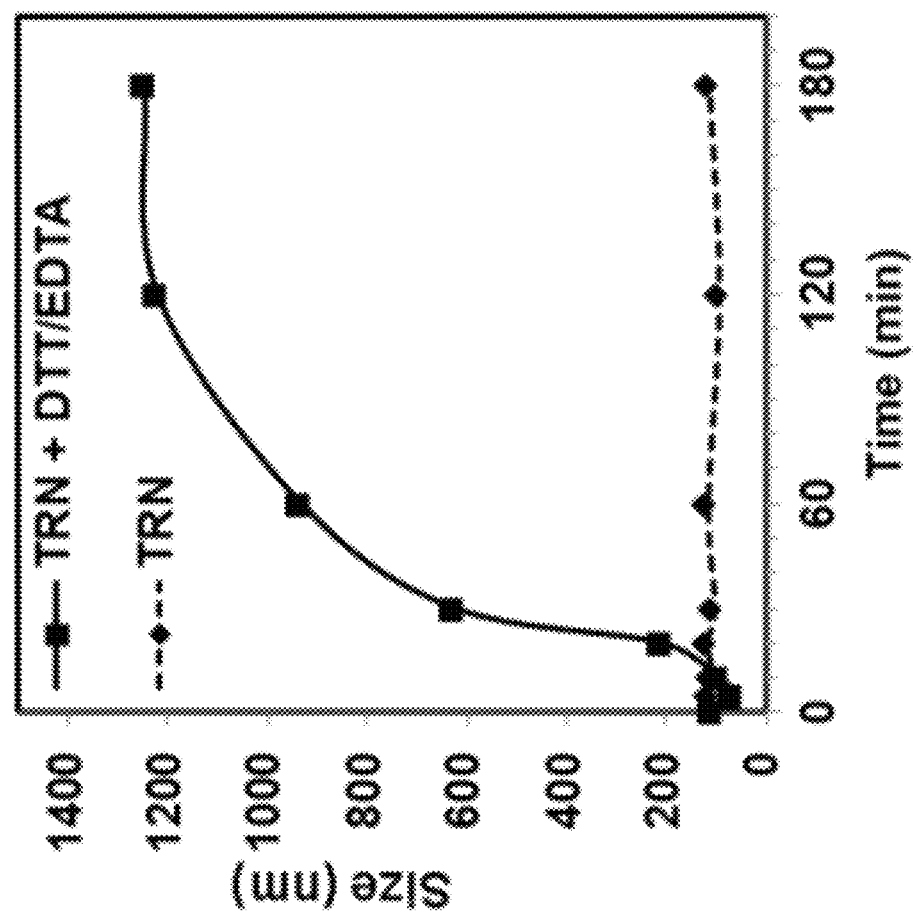
FIG. 4C shows the z-average size of TRN in response to the addition of 10 mM DTT, according to the Examples.

DLS revealed that the size of PDA-PEG-NiPMA is sensitive to pH, redox potential, and temperature. PDA-PEG-NiPMA nanogel increases its size from 99 nm to 203 nm upon the decrease in pH from 7.4 to 5.0 (FIG. 2), then further expands to 360 nm in 16 h. Furthermore, we also found that the increase of temperature significantly increased nanogel size (FIGS. 4A and 4B). In addition, the size of nanogel increases dramatically with the addition of dithiothreitol (FIG. 4B and 4C). Due to this unique size-expanding property to stimuli, the PDA-PEG-NiPMA nanogel was named as triple responsive nanogel (TRN).

II. Sub-Cellular Localization of Pc 4-TRN

PS targets three main organelles: mitochondria, ER and lysosomes. Pc 4 binds preferentially to mitochondria and ER, mitochondria targeting being particularly important in cell killing. Our published work also shows that releasing iron from lysosomes markedly enhances mitochondria-mediated Pc 4-PDT toxicity in UMSCC22A cells. Since NP are taken up by cells via endocytosis, we assessed sub-cellular localization of Pc 4-TRN in UMSCC22A cells. Cells were incubated with 200 nM Pc 4-TRN (blue) for 1, 2 and 20 h and subsequently co-loaded with LysoTracker Green (LTG, green) and tetramethylrhodamine methylester (TMRM, red) to label endosomes/lysosomes and mitochondria, respectively. After 1 h, the presence of small round green/light cyan spheres representing lysosomes indicate that Pc 4-TRN began to enter the lysosomes but no co-localization of Pc 4-TRN with mitochondria was observed. After 2 h, the size of many cyan lysosomes increased supporting our hypothesis that TRN expands due to acidic lysosomal pH/higher lysosomal redox potential compared to extracellular fluid, as our in vitro experiment shows. After 20 h, LTG fluorescence became diffuse, indicating that most lysosomes have broken down. Also, TMRM fluorescence changed from red to magenta, indicating strong co-localization between mitochondria and Pc 4. Collectively, these pilot experiments suggest that once TRN are taken up by endosomes/lysosomes, they self-expand and degrade in acidic environment resulting in breakage of lysosomal membranes, allowing free Pc 4 and other lysosomal constituents, such as iron, to be released from lysosomes and transport to mitochondria.

III. MBA Effect in Cellular Uptake and Cell Killing

NPs are taken up by cells through endocytic pathway, which is efficient way to increase intracellular NP concentration. To further enhance their payload, NP can be decorated with specific molecular motifs that facilitate active binding of NP to plasma membrane for further internalization. Many tumors highly express sigma 2 receptor. Therefore, we formulated the TRN with a ligand (MBA) that binds to sigma 2 receptor on plasma membrane of cancer cells, and tested its efficacy to kill UMSCC22A cells. Confocal microscopy revealed that TRN with MBA moieties entered UMSCC22A cells faster than its non-targeted counterpart, suggesting MBA corresponding receptor mediated endocytosis. After 2 h incubation, MBA-Pc 4-TRN-PDT was more effective in killing cells compared to without MBA motif (100% vs. 50% killing at 6 h) (FIG. 6B), which further subsidize our hypothesis. The results indicate that MBA targeting motif enhances TRN uptake and killing efficacy during PDT.

IV. Biodistribution of MBA-Pc 4-TRN

Xenografts were created with UMSCC22A cells (3×10⁶ cells/mouse) in male athymic Nu/J mice (6 weeks old, inbred homozygous) (Jackson Labs). Once tumor volumes reached 50-150 mm³ measured with a caliper, mice were administered with MBA-Pc 4-TRN (1 mg/kg Pc 4) in PBS through the tail vein. Fluorescence images were taken with an in vivo fluorescence imaging system (CRI Maestro 2) 72 h after MBA-Pc 4-TRN dosing. Subsequently, mice were sacrificed at 96 h post-injection. Liver, spleen, heart, kidneys, lungs, and the tumor were collected and imaged. At 72 h post-injection, MBA-Pc 4-TRN signal mainly appeared in the regions of tumor and liver, some in the bladder but very little in other tissues. Significantly different from other Pc 4 loaded carrier systems, there was almost no skin associated Pc 4 signal observed. Furthermore, the ex vivo images obtained from dissected organs at 96 h post Pc 4 injection revealed that the majority of MBA-Pc 4-TRN was still enriched in the tumor, while liver showed much less fluorescence compared to 72 h time point. As expected, spleen, heart, lungs and kidney retained very little Pc 4.

Example 2

In Vitro and In Vivo Examples were Performed Using the Materials of Example 1

I. Pc 4 Nanogel Drug Concentration Determination and Release Kinetic Assay

Pc 4 shows maximum absorbance at peak 670 nm. Therefore, Pc 4 concentration in nanogels was measured at 670 nm by UV-Vis spectroscopy. Pc 4 nanogel 2 µL was diluted with 980 µL DMSO (diluted 50×) and measured by UV-Vis. Drug concentration was then calculated by calibration curve. Pc 4-TRN was suspended in PBS of pH 7.4 (10 mM) at the final concentration of 10 µg/mL. To mimic the drug release process of Pc 4-TRN during blood circulation and inside lysosome, Pc 4-TRN was dialyzed towards 40 mL PBS (pH 7.4, 10 mM, 1% Tween 80) and acetate buffer (pH 5.0, 1% Tween 80) at 37° C., respectively. At pre-determined time intervals, 1 mL dialysis buffer was removed and replaced with 1 mL fresh buffer. The samples were stored at −20° C. till measurement. After collecting all samples, 100 µL each sample was loaded into 96 well plate (Costar, black, clear bottom) and Pc 4 concentration was quantified by fluorescence (Ex 610 nm, Em 680 nm, SpectraMax M2 Multi-Mode Microplate Reader). A calibration curve was constructed by adding known concentrations of Pc 4 to PBS pH 7.4 (10 mM, 1% Tween 80) acetate buffer (pH 5.0, 1% Tween 80). To simulate the process of Pc 4-TRN escaping from lysosome and transfer to cytosol, the pH of releasing buffer was adjusted to 5.0 at first 2 h. After that, the pH of the releasing buffer was adjusted to 7.2 and kept at this pH for remaining experiment, GSH (final concentration was 10 mM) was added into the buffer at the same time. As a control group, no GSH was added into buffer; however, the pH of the buffer was also adjusted to 7.2 and kept at this pH for the remaining experiment. At pre-determined time intervals, samples were retreated and Pc4 concentration was measured by fluorescence as previously described.

II. Cellular Uptake of TRN Observed by Confocal Microscopy

UMSCC22A cells (200,000 cells/dish) were cultured on 35 mm2 Petri dishes (MatTek, MA, USA) for overnight. The media were replaced with fresh media containing 16% MBA-Pc 4-TRN, Pc 4-TRN, and free Pc 4 (equivalent to 200 nM Pc 4). After 4 or 20 h of incubation under a humidified atmosphere of 95/5% air/CO2, cells were washed by PBS (3×), fixed with formaldehyde (4.5% in PBS) and stained with Hoechst 33342 (final concentration 1 µg/mL). Then cells were analyzed under a confocal microscope (LSM 510, Carl-Zeiss Inc.)

III. Quantification of Intracellular Pc 4 Amount

UMSCC22A cells (100,000 cells/well) were cultured on 24-well plate for overnight. Culture media were replaced with fresh media containing free Pc4 drug, MBA (16, 8, 4, 1, and 0%) Pc 4-TRN nanogels (equivalent to 200 nM Pc 4). After incubation under a humidified atmosphere of 95/5% air/CO2 for 4 and 20 h, respectively, cells were washed by PBS (3×) and lysed in 0.5% SDS. Cell lysates were collected and Pc 4 concentration was quantified by fluorescence (Ex 610 nm, Em 680 nm). Total protein concentrations of cell lysates were measured by BCA kit following manufacturer's instruction (Thermo Fisher Scientific). The ratio between Pc 4 and protein was used to evaluate the ability of UMSCC22A cells take up Pc 4 and Pc 4-TRN of different MBA density.

IV. Immunohistochemistry Analysis

Human tissues were collected under IRB protocol approved by the Institutional Review Board of the Medical University of South Carolina. FFPE sections of human head and neck tumor tissue microarray were de-paraffinized in xylene, rehydrated in alcohol, and processed as follows: The sections were incubated with target retrieval solution (Dako S2368) in a steamer (Oster CKSTSTMD5-W) for 45 min, 3% hydrogen peroxide solution for 10 min and protein block (Dako X0909) for 20 min at room temperature. After overnight incubation with sigma-2 antibody (Sigma HPA002877) in a humid chamber at 4° C., biotinylated anti-rabbit secondary antibody (Vector, PK-6101) and ABC reagent (Vector, PK-6101) was added for 30 min. Immunocomplexes of horseradish peroxidase were visualized by DAB (Dako, K3468) reaction, and sections were counterstained with hematoxylin before mounting.

V. Western Blot Analysis

UMSCC22A cell extracts were prepared in ice-cold RIPA lysis buffer (150 mM NaCl, 1 mM EGTA, 1% sodium deoxycholate, 1% Triton X-100, 0.1% SDS, 1% NP40, 50 mM Tris-Cl, pH 7.4) supplemented with a cocktail of protease inhibitors (Roche Diagnostics) and centrifuged. Proteins (75 µg) in sample buffer (Invitrogen) supplemented with 10% SDS and 10% β-mercaptoethanol were resolved on NuPAGE® Tris-bis 4%-12% polyacrylamide gels (Invitrogen). Proteins were transferred to PVDF membranes (EMD Millipore) and probed with anti-sigma-2 (PGRMC1) (1:1000) (Cell Signaling). Membranes were developed by the Enhanced Chemiluminescence Detection System (Thermo Fisher Scientific), and band intensities were quantified using a Carestream 4000 PRO image station (Woodbridge, Conn.).

VI. Sub-Cellular Co-Localization of TRN

UMSCC22A cells (150,000 cells/dish) were cultured onto glass-bottomed MatTek dishes and incubated with MBA-Pc 4-TRNs at indicated times. Before imaging, medium was changed to fresh medium supplemented with Insulin-Transferrin-Selenium-X (ITX) reagent [insulin (10 µg/m), transferrin (5.5 µg/m), selenium (6.7 ng/ml), ethanolamine (0.2 mg/ml)] (Gibco) but omitting FBS. To assess co-localization of nanoparticles with mitochondria, cells were loaded with 500 nM tetramethylrhodamine methylester (TMRM). Medium was then changed with fresh medium containing 50 nM TMRM. To assess co-localization of MBA-Pc 4-TRNs with lysosomes, cells were loaded with 500 nM LysoTracker Green (LTG). Dishes were placed in an environmental chamber at 37° C. on the stage of a Zeiss LSM 510 laser scanning confocal microscope (Zeiss, Thornwood, N.Y.). A 63×N.A. 1.4 oil immersion planapochromat objective was used for all experiments. LTG, TMRM and Pc 4 fluorescence was imaged using 488 nm excitation/500-530-nm emission, 543 nm excitation/565-615 nm emission and 633 nm excitation/650-710 nm emission, respectively. ImageJ software was used to post-process the images and calculate the co-localization coefficients.

VII. Photodynamic Therapy

Cell cultures were incubated with 200 nM of MBA-Pc 4-TRN and Pc 4-TRN for 20 h before exposure to 200 mJ/cm2 red light (670 nm) from an Intense-HPD 7404 diode laser (North Brunswick, N.J.). After exposure to red light, cells were incubated for various periods of time prior to analysis.

VIII. Assessment of Cell Death after PDT

Cell death was assessed by propidium iodide (PI) fluorometry using a multi-well fluorescence plate reader, as previously described [16]. Human head and neck cancer cells (UMSCC22A) were plated on 96-well plates (15,000 cells/well) in Dulbecco's Modified Eagle's Medium (DMEM) (Gibco) supplemented with 10% fetal bovine serum (FBS) and penicillin/streptomycin (complete culture medium) in a humidified 37° C. incubator at 5% CO2/95% air. Subsequently, cells were incubated with MBA-Pc 4-TRN and Pc 4-TRN (200 nM) for 20 h. Before exposure to light, cells were changed to fresh medium supplemented with PI (30 µM) and Insulin-Transferrin-Selenium-X (ITX) reagent [insulin (10 µg/ml), transferrin (5.5 µg/m), selenium (6.7 ng/ml), ethanolamine (0.2 mg/ml)] (Gibco) but omitting FBS. PI fluorescence was measured at frequent intervals using 530 nm excitation (25 nm band pass) and 620 nm emission (40 nm band pass) filters. Between measurements, microtiter plates were placed in a 37° C. incubator. At the end of the experiment, digitonin (200 µM) was added to each well to permeabilize all cells and label all nuclei with PI. Cell viability determined by PI fluorometry is essentially the same as cell viability determined by trypan blue exclusion.

IX. Biodistribution of MBA-Pc 4-TRN

All animal experiments followed the protocols approved by the MUSC Institutional Animal Care and Use Committee (IACUC). Head and neck tumor xenografts were created with UMSCC22A cells (3×106 cells/mouse) in male athymic Nu/J mice (6 weeks old, inbred homozygous) (Jackson Labs). Once tumor volumes reached 50-150 mm$^3$ measured with a caliper, mice were administered with MBA-Pc 4-TRN and free Pc 4 (1 mg/kg Pc 4) in PBS through the tail vein. Fluorescence images were taken with a Maestro 2 in vivo imaging system 72 h after dosing. Subsequently, mice were sacrificed at 96 h post-injection. Liver, spleen, heart, kidneys, lungs, and the tumor were collected and imaged.

X. Results

Figure 3:
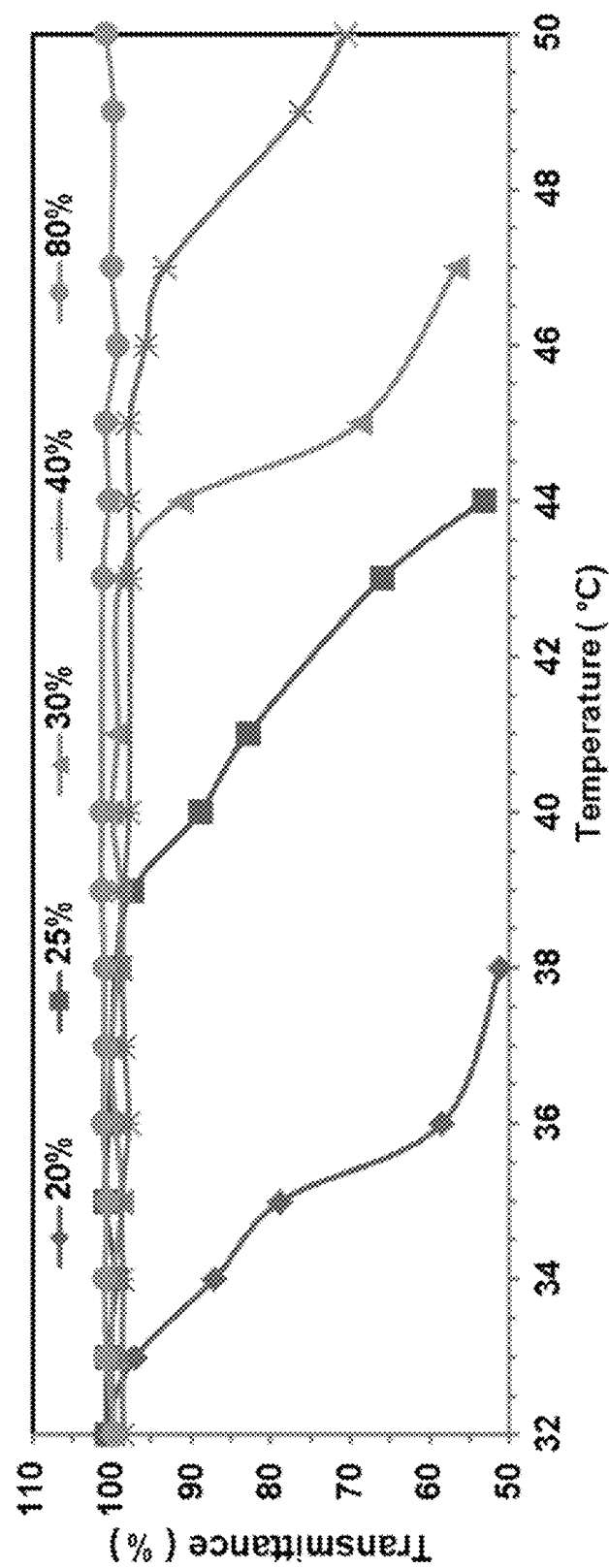
FIG. 3 shows the relationship between TRN crosslinking density and its transition temperature. The transition temperatures were determined by measuring the change of transmittance for TRN PBS suspension at the nanogel concentration of 0.16 mg/ml during the increase of temperature, according to the Examples.

PNiPMA is a polymer which undergoes phase transition when the environmental temperature passing through its Low Critical Solution Temperature (LCST, around 43° C.), soluble in water at temperature lower than LCST while becoming hydrophobic at temperature higher than its LCST. Nano/micro-particles containing PNiPMA shrink when the environment temperature is higher than its LCST. To investigate the effect of crosslinking density (CD) of TRN on its transition temperature, the transmittance of TRN was recorded during the course of temperature increase. Transmittance measurement revealed that the addition of PNiPMA did endow the temperature sensitivity to the nanogel: TRN nanogel suspension decreased its transmittance and appeared cloudy at high temperature (FIG. 3). The transition temperature of TRN shifted from 30.5° C. to 47° C. as its CD increased from 20 to 40%, while no transition was recorded for TRN with 80% CD or higher. Therefore, TRNs with different transition temperatures can be attained by simply tuning CD during nanoparticle fabrication process.

Using the fabrication protocol described above, Pc 4 loaded TRN with a transition temperature slightly higher than body temperature can be easily produced from PDA-PEG-PNiPMA with 30% CD. Compared with its counterpart fabricated from PDA-PEG polymer, the loading efficiency of Pc 4 increased from 13 to 40% for TRN, which maybe due to the newly formed PNiPMA layer served as a buffer zone between the hydrophobic PDA and the hydrophilic PEG. To investigate how the TRN responses to the changes in temperature, redox potential, and pH after the loading of Pc 4, the sizes and morphologies of the TRN were measured with dynamic light scattering (DLS) and observed with transmittance electron microscopy (TEM), respectively. The size of the TRN was 108.1±11.1 nm with a PDI of 0.163 (FIG. 4A). Zeta sizer found that TRN carried slightly negative surface charge (−5.62±1.40 mV). TEM revealed that TRNs were spherical. TRN itself was stable in PBS and culture medium containing 10% FBS, and no obvious size change was observed after 3 days of incubation. In contrast to its PDA-PEG di-copolymer nanogel counterpart, which kept constant size in the whole tested temperature range, TRN with 30% CD dramatically increased its size at temperature higher than 39° C. (FIG. 4A). It is worth noting that the size enlargement in response to the temperature increase is totally different from other PNiPMA containing particles, which shrink upon environment temperature higher than their LCSTs. FIG. 4A also showed that the addition of Pc 4 slightly decreased the transition temperature of TRN from 44° C. to 39° C. The enlarged size of TRN also evidenced the thermal expanding property of TRN.

To examine the redox potential effect on the transition temperature of TRN, 10 mM DTT was added during the heating process. To eliminate the possible effect caused by the intra-particle crosslinking of TRN after DTT treatment shown in FIG. 4B, EDTA was added. FIG. 4B revealed that the addition of 10 mM DTT/EDTA further decreased the transition temperature of TRN from 39° C. to 36° C. It is known that cytosol has an elevated glutathione level (10 mM, much higher than that in the blood), which would result in the rapid intracellularly self-expanding of TRN at body temperature.

Figure 2:
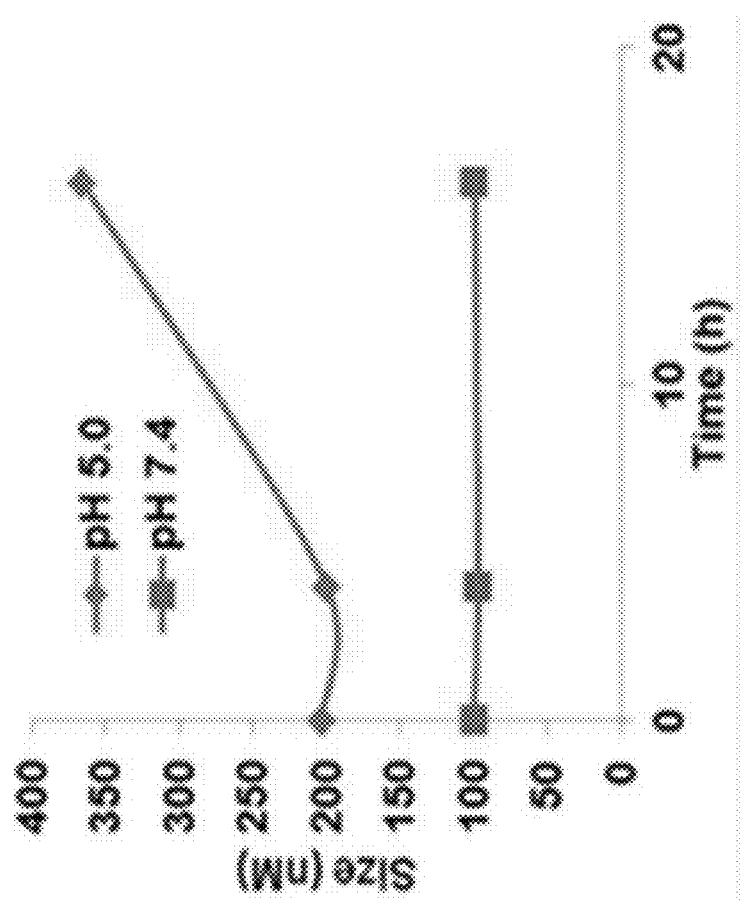
FIG. 2 shows the hydrodynamic size of Pc 4-TRN in response to a change in pH, according to the Examples.
Figure 4D:
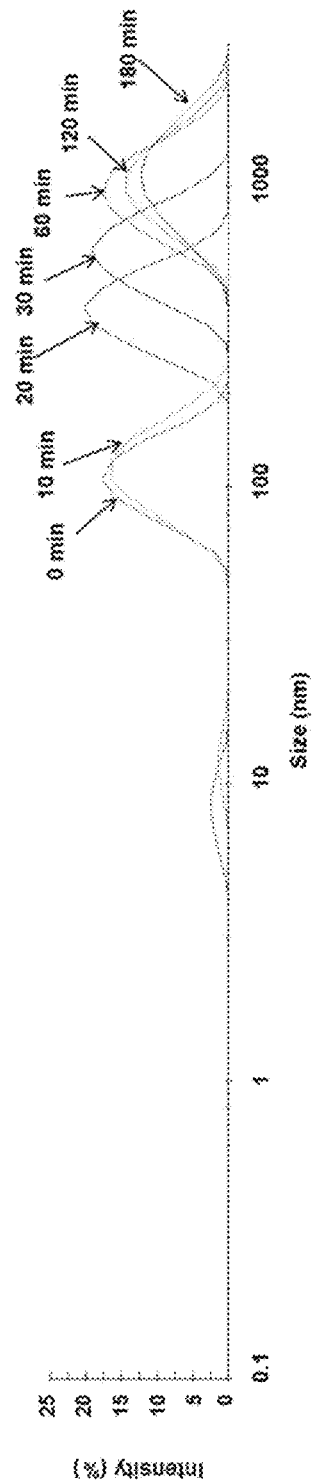
FIG. 4D shows the size distribution of TRN in response to the addition of 10 mM DTT over time, according to the Examples. For all of FIGS. 4A-4D, the size measurements were carried out at 37° C. unless otherwise specified.

To further evaluate the sensitivity of TRN in response to reducing environment at body temperature, the size of TRNs suspended in media with or without 10 mM DTT/EDTA was monitored at 37° C. As we expected, the size of TRN remained constant in PBS buffer (FIG. 4C). To our surprise, under reducing environment, TRN swelled from 108 nm to 627 nm in 30 min and further expanded to larger than 1200 nm in less than 2 h (FIG. 4D), achieving more than 1000-fold size enlargement (in volume), which is more than 10-fold faster than its di-copolymer counterpart. Besides its self-expansion in response to the increase of temperature and redox potential, DLS and TEM also revealed that the size of TRN was also sensitive to the change of pH. TRN instantly expanded its size from 108 nm to 203 nm upon the decrease of pH from 7.4 to 5.0, and then further increased to 360 nm in 16 h (FIG. 2).

To verify that the stimuli triggered size enlargement of TRN will result in faster release of Pc 4, drug release assay was carried out in pH 7.4 and 5.0 buffers to mimic the extracellular and lysosomal environments, respectively. TRN released only 13.6% of Pc 4 in pH 7.4 buffer over 3 days of incubation, indicating that TRN is a stable carrier during the circulation. As we expected, the release of Pc 4 became much faster in the pH 5.0 environment (30.7% Pc 4 released in 24 h). To investigate the effect of redox potential sensitiveness of TRN on its payload release, TRN was first incubated in pH 5.0 medium for 2 h and then transferred to pH 7.2 medium supplemented with 10 mM GSH to mimic the process of TRN escaping from lysosome to cytosol. It was found that the addition of GSH significantly accelerated the drug releasing process.

Figure 5B:
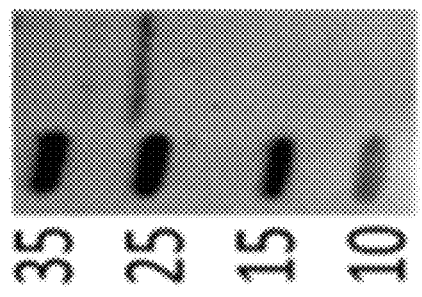
FIG. 5B shows the expression of sigma-2 receptor in UMSCC22A cell line detected by Western immunoblotting, according to the Examples.
Figure 5A:
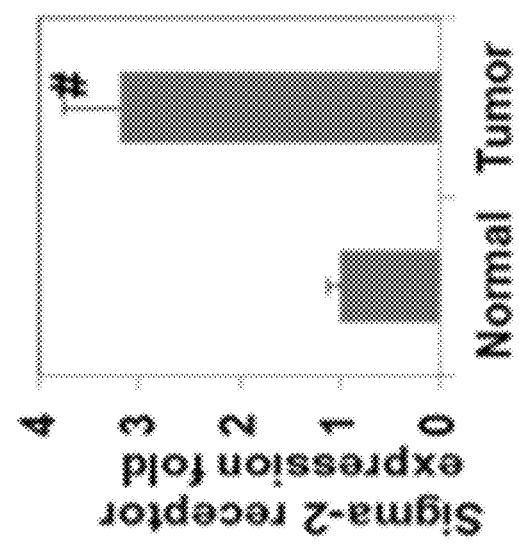
FIG. 5A shows that sigma-2 receptor positive tissue areas were detected with immunohistochemistry and quantified as percent of total tissue and expressed as fold of normal tissue (mean±SE, n>30, # p<0.001), according to the Examples.

Head and neck squamous cell carcinoma (HNSCC) was selected to explore the PDT efficacy of TRN because most HNSCC cases are localized. In addition, the treatment for HNSCC should not compromise the function and cosmetic appearance of corresponding tissues. All these make PDT, which causing minimal scar and loss of function of treated sites, a better alternative for surgery to treat HNSCC. Sigma-2 receptor is overexpressed in many cancers, including skin cancer, lung cancer, and breast cancer, and has been extensively explored as a target for tumor specific drug delivery. However, thus far, no research investigated the expression of sigma-2 receptor in head and neck cancer. The expression of sigma-2 receptor in HNSCC was evaluated with immunohistochemistry in a human tissue array. High density of brown staining in the tumor tissue and little staining in the normal tissue indicated that sigma-2 receptor does overexpress in human head and neck tumor tissue, which makes it a valid target for tumor specific drug delivery. The quantitative analysis of the DAB-stained tissues revealed that human HNSCC expressed >3-fold of sigma-2 receptor than normal tissues (FIG. 5A). After that, we further confirmed that sigma-2 receptor is expressed in UMSCC22A head and neck cancer cells by Western immunoblotting (FIG. 5B). Thus, UMSCC22A cell line was selected to validate our hypothesis in vitro.

Figure 5C:
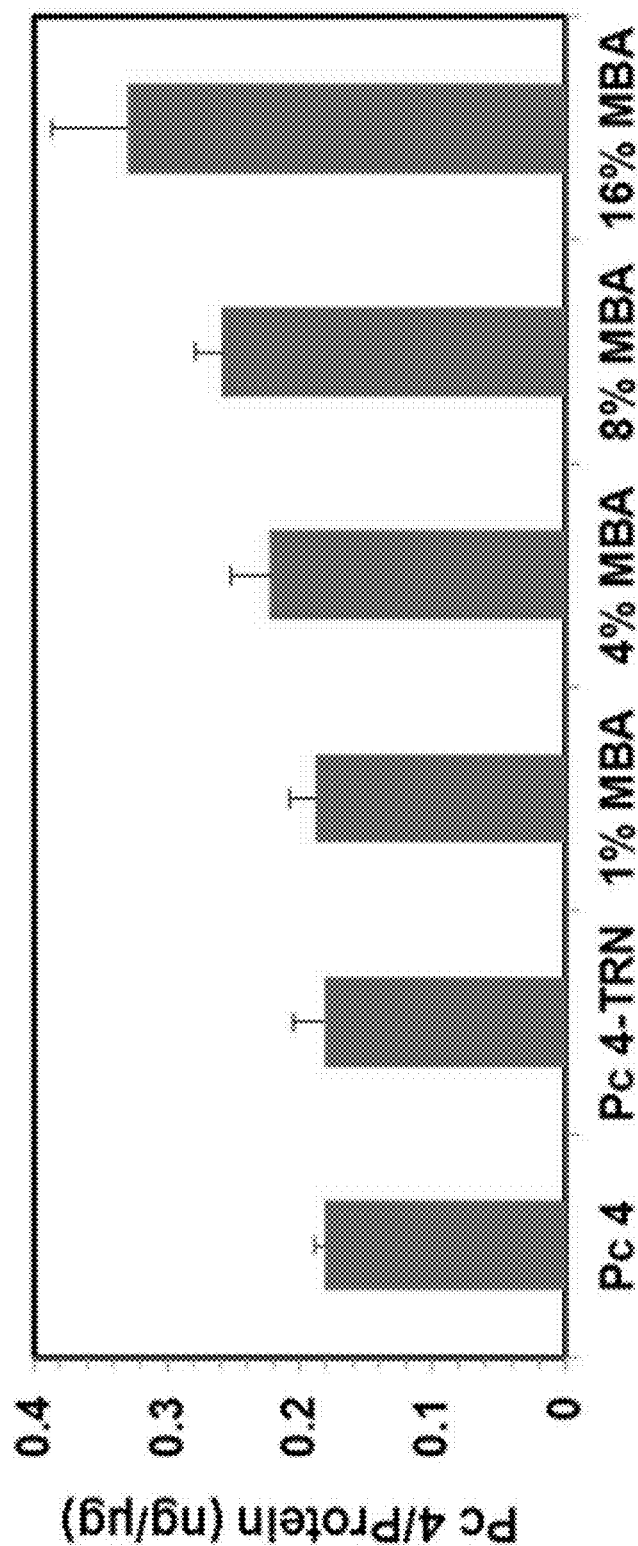
FIG. 5C shows the intracellular amount of Pc 4 for cells treated with Pc 4-TRNs containing different MBA densities (mean±SD, n=3), according to the Examples.

To endow head and neck tumor targeting effect for TRN, a sigma-2 receptor targeting ligand, 4-methoxybenzoic acid (MBA), was grafted onto PDA-PEG-PNiPMA with the help of 1-Ethyl-3-[3-dimethylaminopropyl]carbodiimide (EDC) and N-hydroxysuccinimide (NHS) (FIG. 1B). MBA-Pc 4-TRNs with different MBA densities were fabricated by adjusting the molar ratio of MBA-PDA-PEG-PNiPMA to PDA-PEG-PNiPMA. To investigate the targeting effect of MBA on the cellular uptake of Pc 4 loaded TRN, confocal microscopy was employed. Red fluorescence signal (Pc 4) was observed among all treatments. Compared with free Pc 4, non-targeted TRN showed similar capacity in carrying Pc 4 into UMSCC22A cells during 20 h of incubation. As we expected, the functionalization of TRN with MBA significantly enhanced its cellular uptake. To further quantify the intracellular Pc 4 amount after 20 h of incubation, the cells were harvested and lysed to measure the intracellular Pc 4 amount. MBA-TRN with 16% ligand density achieved about 1.8-fold of Pc 4 uptake compared with that of non-targeted TRN (FIG. 5C). The higher the MBA density, the better its cellular uptake, which suggest that the modification of MBA did facilitate the sigma-2 receptor mediated endocytosis for Pc 4 loaded TRN.

Figure 6A:
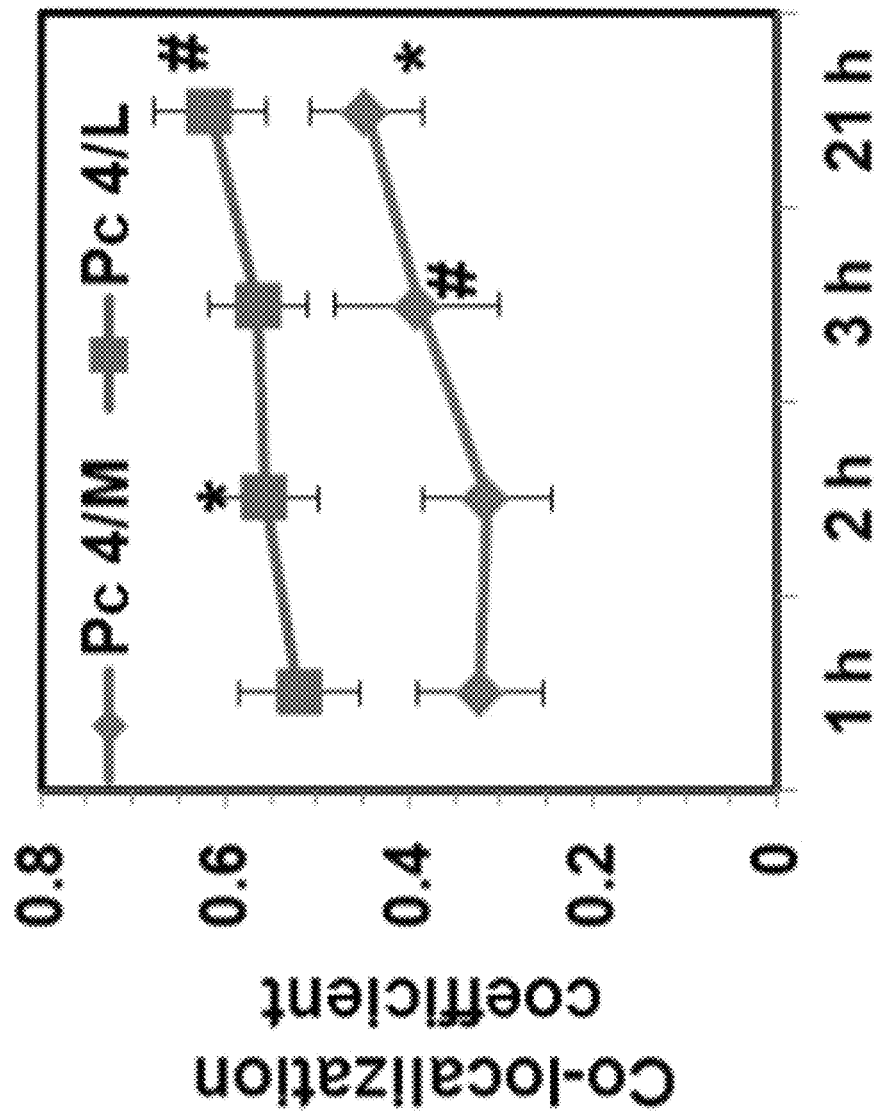
FIG. 6A shows the trend for the Pc 4 co-localizing with lysosome (Pc4/L) and mitochondria (Pc 4/M) (mean±SD, n>15; *p<0.05; # p<0.01), according to the Examples.

Since TRN was taken up by cells via endocytosis, we assessed the sub-cellular localization of MBA-Pc 4-TRN in UMSCC22A cells after it entered cells by confocal microscopy. Cells were incubated with 200 nM Pc 4-TRN (blue) for 2, 3, and 20 h and subsequently co-loaded with LysoTracker Green (LTG, green) and tetramethylrhodamine methylester (TMRM, red) to label endosomes/lysosomes and mitochondria, respectively. After 2 h, the presence of small round green/light cyan spheres representing lysosomes indicate that Pc 4-TRN began to enter the lysosomes but very few co-localization of Pc 4-TRN with mitochondria (red) was observed. After 3 h, much more cyan spheres appeared, suggesting more TRN entered lysosomes; furthermore, the color of mitochondria turned from red to magenta, indicating strong co-localization between mitochondria and Pc 4. After 21 h, blue fluorescence became diffused, showing the expanding of TRN resulted in the release of Pc 4. Moreover, mitochondria exhibited stronger magenta fluorescence, indicating more Pc 4 transferred to mitochondria. It is also worth mentioning that we also observed some enlarged lysosome, suggesting the expanding of TRN inside the lysosome during its intracellular traffic. To further quantitatively monitor the intracellular trafficking of TRN, images (n>15) taken at different time points were analyzed by ImageJ to calculate the Pearson's co-localization coefficient for lysosome and Pc 4 (Pc 4/L), as well as Pc 4 and mitochondria (Pc 4/M). FIG. 6A shows that more TRNs entered lysosomes after 2 h of incubation than that of 1 h ($p<0.05$). The stronger co-localization of Pc 4 and mitochondria occurred after 3 h of incubation ($p<0.01$). Since more TRN entered cancer cells after 20 h of incubation, the co-localization of Pc 4/L further increased; as a consequence, more Pc 4 partitioned to mitochondria after it was freed from TRN.

Figure 6B:
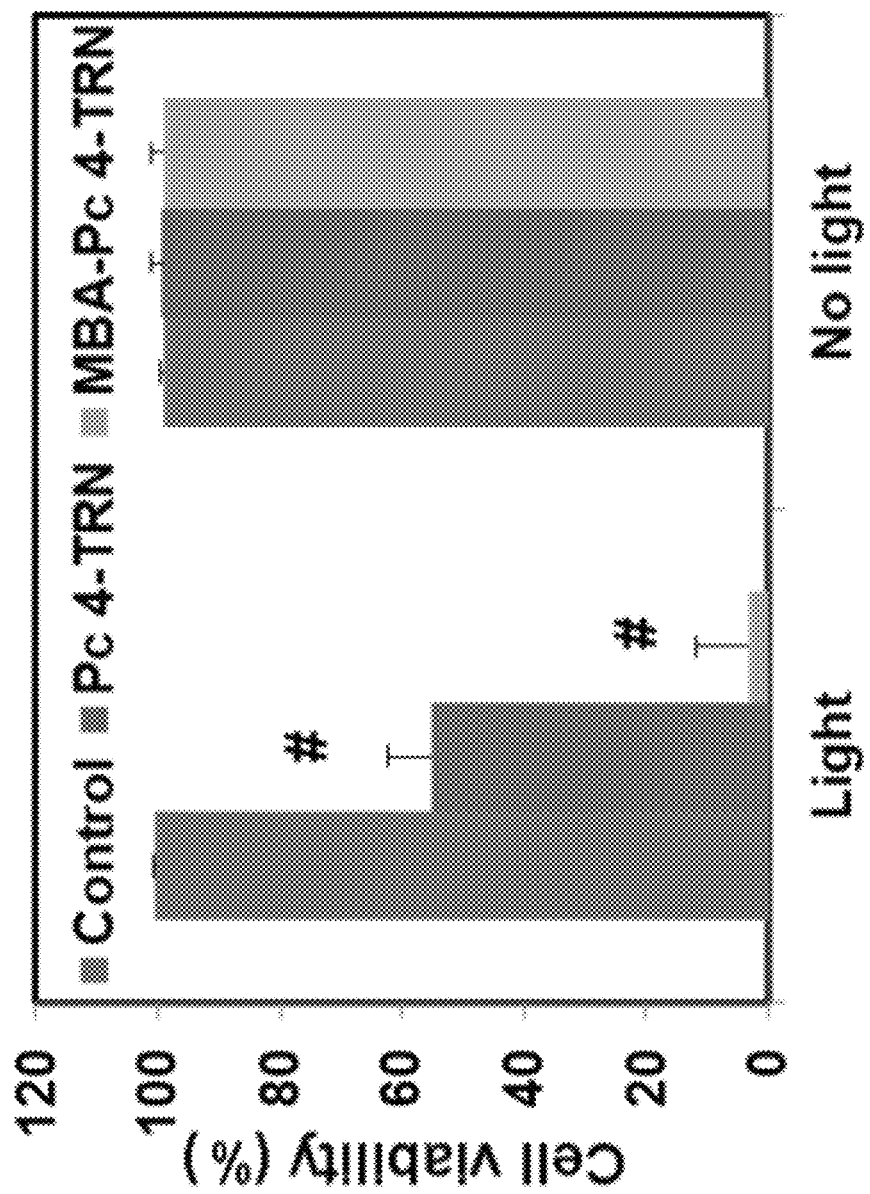
FIG. 6B shows the PDT efficacy in killing UMSCC22A cells 12 h after irradiation (mean±SD, n=3; # p<0.01), according to the Examples.

To validate whether the enhanced uptake of Pc 4 and effective mitochondria targeting could be translated into better PDT efficacy in cell killing, cell viability after PDT was assessed by propidium iodide (PI) fluorometry. UMSCC22A cells were incubated with non-targeted and targeted Pc 4-TRN for 20 h prior to receiving PDT. Cells treated with the same dose of nanoparticle receiving no light were employed as control. FIG. 6B showed that PDT of MBA-Pc 4-TRN killed almost all cancer cells 12 h post irradiation, while only 44.5% cells were killed in the non-targeted TRN treated group. Combining cellular uptake data, we concluded that better cellular uptake of Pc 4 did translate into better PDT cell killing efficacy. Furthermore, no cytotoxicity appeared in either TRN groups without applying light irradiation, indicating MBA-Pc 4-TRN and nano-carrier itself were safe.

To evaluate the tumor specific targeting effect of MBA-Pc 4-TRN, head and neck cancer xenograft mice model was employed. Mice were administered with MBA-Pc 4-TRN through the tail vein injection. Fluorescence images were taken with an in vivo fluorescence imaging system. At 72 h post-injection, MBA-Pc 4-TRN signal mainly appeared in the regions of tumor and liver, some in the bladder but very little in other tissues. The ex vivo images obtained from dissected organs at 96 h post Pc 4 injection revealed that the majority of MBA-Pc 4-TRN was still retained in the tumor, while liver showed much less fluorescence signal compared to that of 72 h time point. As expected, spleen, heart, lungs and kidney retained very little Pc 4, which is significantly different from other Pc 4 loaded carrier systems.

XI. Discussion

Figure 7:
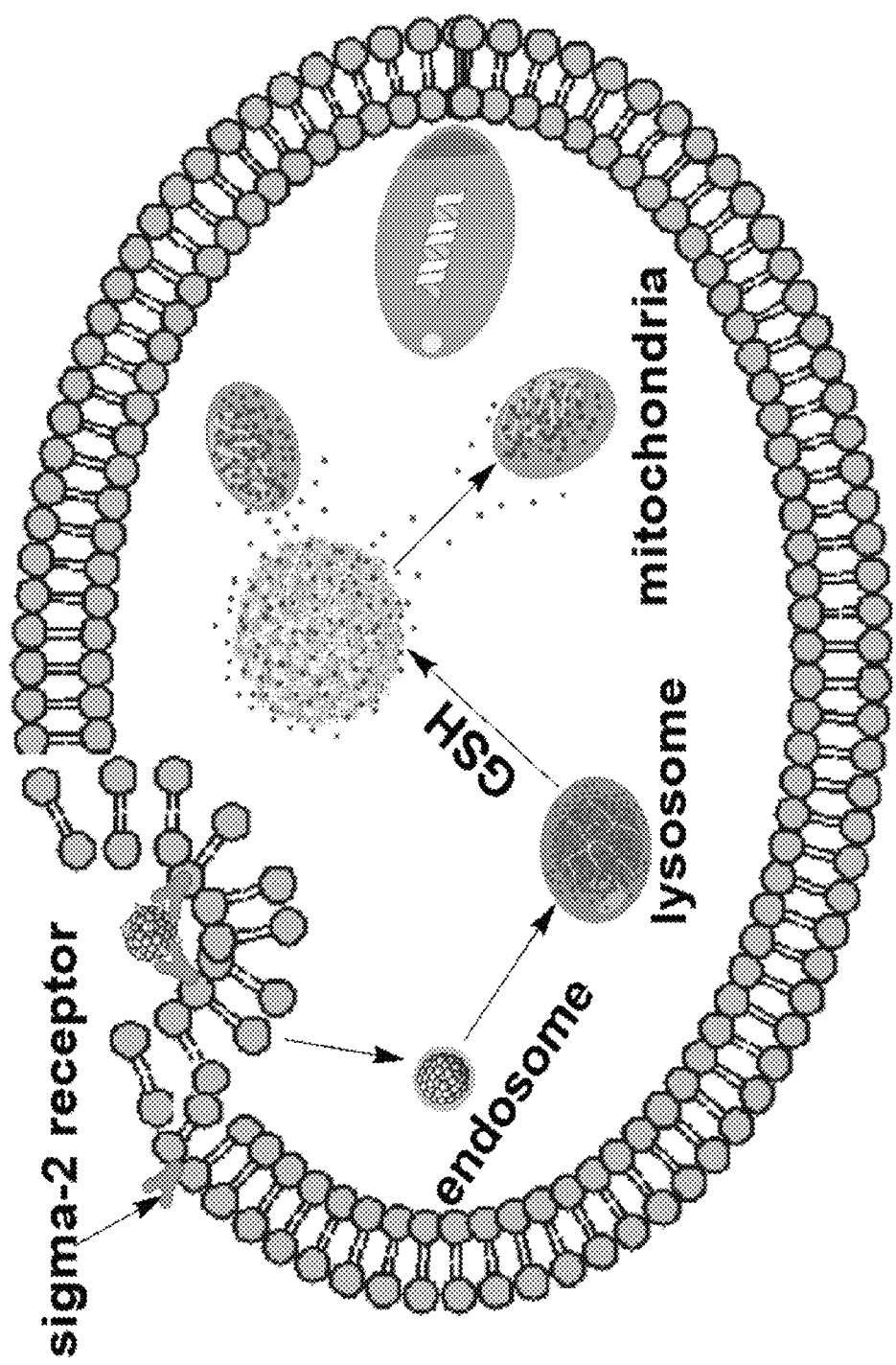
FIG. 7 shows the proposed pathway for MBA-Pc4-TRN into a cell.

PDT causing minimal scar and loss of function of treated sites, has been proposed as an alternative for surgery to treat HNSCC. However, the clinical application of PDT has been hindered due to the poor water solubility and non-specific skin retention of PS, as well as low PDT efficacy. To address that, we designed a thermal, pH, and redox potential triple-responsive expansile nanogel system (TRN), which swells at a temperature higher than its transition temperature, acidic pH, and reducing environment. In vivo biodistribution experiment revealed that TRN could specifically target tumor tissue with the synergetic outcome of EPR effect and sigma-2 receptor targeting effect. The immunohistochemistry analysis of HNSCC human tissue array found that human HNSCC expressed >3-fold of sigma-2 receptor than normal tissues (FIG. 5C). In addition, Western immunoblotting confirmed that sigma-2 receptor is expressed in UMSCC22A head and neck cancer cells (FIG. 5B), which makes UMSCC22A cell line a valid model for the study of sigma-2 receptor targeted therapy. The proposed pathway for MBA-Pc 4-TRN is described in FIG. 7. FIG. 5C proved that MBA-TRN entered head and neck cancer cells by sigma-2 receptor mediated endocytosis with the help of sigma-2 receptor ligand, MBA. After that, MBA-TRN was transferred to endosome and then lysosome, where it has low pH. Partial of Pc 4 could be released from TRN due to the acidic pH. Due the proton sponge effect of pyridine segments in PDA and the expansile property of TRN at low pH, TRN and freed Pc 4 could escape from lysosome and enter cytosol. Since cytosol has an elevated GSH concentration, which can trigger the dramatic size expansion of TRN (FIGS. 4C, 4D) and induce the release of Pc 4. Due to its hydrophobicity, Pc 4 spontaneously transferred to mitochondria (FIG. 6A). Therefore, MBA-Pc 4-TRN exhibited enhanced cell killing effect after PDT (FIG. 6B).

XII. Conclusions

In summary, a thermal, pH, and redox potential triple-responsive expansile nanogel system (TRN) has been developed. The transition temperature of TRN could be tuned from 30.5° C. to 47° C. by adjusting its crosslinking density. Due to the synergistic effect of its redox potential and thermal responsiveness, TRN could expand from 108 nm to over 1200 nm within 2 h in a reducing environment at body temperature, achieving more than 1000-fold size enlargement (in volume). Pc 4 loaded TRNs are stable (both size and retaining loaded drug) in a physiological condition, while quickly releasing Pc 4 at lysosomal pH and reducing cytosol environment attributed to its rapid swelling response upon the trigger of acidic pH, high temperature, and elevated GSH. MBA functionalized Pc 4-TRN could effectively enter UMSC22A cancer cells with the help of sigma-2 receptor and transfer Pc 4 to its target, mitochondria. Consequently, PDT of MBA-Pc 4-TRN showed significant higher toxicity than its non-targeted counterpart and killed almost all cancer cells. Furthermore, in vivo biodistribution study proved that MBA-Pc 4-TRN could effectively target head and neck tumor tissue and be retained there for 4 days. Based on the unique responsiveness and promising in vitro and in vivo results from TRN, further studies will focus on the mechanisms for TRN escaping from lysosome and employing the system for in vivo tumor growth inhibition effect for head and neck cancer.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A thermal triple-responsive polymer, comprising: poly[(2-(pyridin-2-yldisulfanyl)-co-[poly(ethylene glycol)]-co-[N-isopropyl methacrylamide], which contains redox potential sensitive disulfide bonds and acid pH sensitive ester bonds and further contains temperature sensitive segments.

2. The thermal triple-responsive polymer as in claim 1, having the structure:

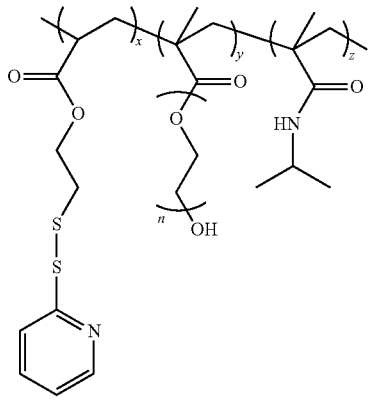

where
x is about 3 to about 500;
y is about 3 to about 500;
n is about 3 to about 200; and
z is about 3 to about 500.

3. The thermal triple-responsive polymer as in claim 1, having a weight average molecular weight of about 5,000 Da to about 500,000 Da.

4. The thermal triple-responsive polymer as in claim 3, having a polydispersity of about 1.1 to about 2.5.

5. The thermal triple-responsive polymer as in claim 1, formed via free radical polymerization of 2(pyridin-2-yldisulfanyl)ethyl acrylate, polyethylene glycol) methacrylate, and N-isopropyl methacrylamide with an initiator.

6. The thermal triple-responsive polymer as in claim 5, wherein the initiator comprises 2,2-azobisisobutyronitrile.

7. A photosensitizer loaded nanogel comprising:
the thermal triple-responsive polymer of claim 1; and
a photosensitizer.

8. The thermal triple-responsive polymer as in claim 1, modified with 4-methoxybenzoic acid to endow tumor targeting effect.

9. The thermal triple-responsive polymer as in claim 7, having the structure:

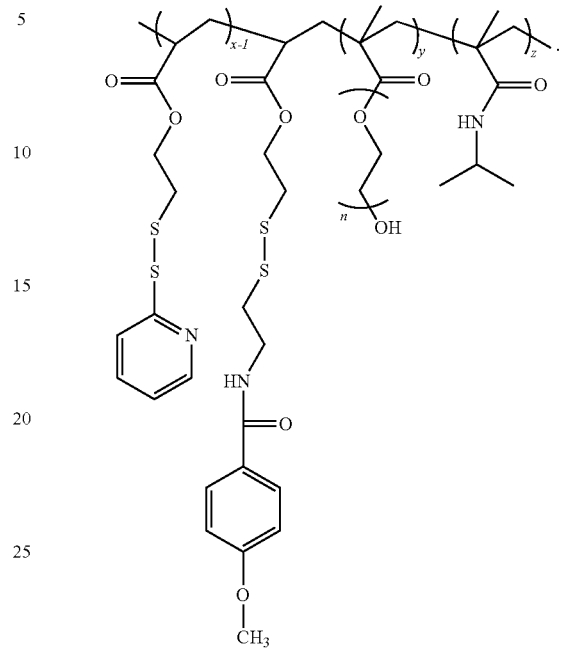

10. A photosensitizer loaded nanogel comprising:
the thermal triple-responsive polymer of claim 8; and
a photosensitizer.

11. A method of forming a nanogel, comprising:
reacting the thermal triple-responsive polymer of claim 1 with a crosslinker and a photosensitizer.

12. The method as in claim 11, wherein the thermal triple-responsive polymer comprises poly[(2-(pyridin-2-yldisulfanyl)-co-[poly(ethylene glycol)]-co-[N-isopropyl methacrylamide] modified with 4-methoxybenzoic acid.

13. The method as hi claim 11, wherein the crosslinker comprises tris(2-carboxyethyl)phosphine hydrochloride.

14. The method as in claim 11, wherein the photosensitizer comprises a silicon phthalocyanine photosensitizer.

* * * * *